United States Patent [19]

Takashita et al.

[11] Patent Number: 5,331,855
[45] Date of Patent: Jul. 26, 1994

[54] ULTRASONIC INSPECTION SYSTEM

[75] Inventors: Yoshihiko Takashita; Souji Sasaki, both of Ibaraki, Japan

[73] Assignee: Hitachi Construction Machinery Co., Ltd., Japan

[21] Appl. No.: 886,381

[22] Filed: Feb. 4, 1992

Related U.S. Application Data

[63] Continuation of PCT/JP90/00754, Jun. 8, 1990.

[30] Foreign Application Priority Data

Aug. 7, 1989 [JP] Japan .................. 1-202807

[51] Int. Cl.⁵ .................. G01N 29/26; G01N 29/10
[52] U.S. Cl. .................. 73/602; 73/625; 73/628
[58] Field of Search .................. 73/602, 618, 620, 625, 73/628

[56] References Cited

U.S. PATENT DOCUMENTS

| | | | |
|---|---|---|---|
| 4,545,251 | 10/1985 | Uchida et al. | 73/628 |
| 4,644,510 | 2/1987 | Fujii | 73/602 |
| 4,699,007 | 10/1987 | Kawashima et al. | 73/625 |
| 4,896,278 | 1/1990 | Grove | 73/602 |

FOREIGN PATENT DOCUMENTS 242355 2/1990 Japan .

*Primary Examiner*—Hezron E. Williams
*Assistant Examiner*—Rose M. Finley
*Attorney, Agent, or Firm*—Wegner, Cantor, Mueller & Player

[57] ABSTRACT

In an ultrasonic inspection system for inspecting the surface condition of an object or the existence or absence of internal defects in it by ultrasonically scanning the object with ultrasonic beams, which have been successively produced as a result of successive excitation of a number of array element oscillators ($10_1$–$10_n$) arranged in a row, and then analyzing waves reflected by the object, reference data for individual ultrasonic beams (individual channels) are collected by ultrasonically scanning a reference material of defect-free uniform quality before ultrasonic inspection of the object. Correction values are prepared based on these reference data, and signals received by the ultrasonic scanning of the object are corrected by these correction values. According to one correction means, the ratios of the average value of reference values of the individual channels to the reference values of the individual channels are determined channel by channel. Using these ratios as correction values, they are multiplied to signals received through the corresponding channels. The products are used as data to be shown on a display unit (21). By these attenuation factors, signals received through the corresponding channels are attenuated at a sensitivity equalizer (31). Scattering in sensitivity among the individual channels can be eliminated by these correction means.

4 Claims, 13 Drawing Sheets

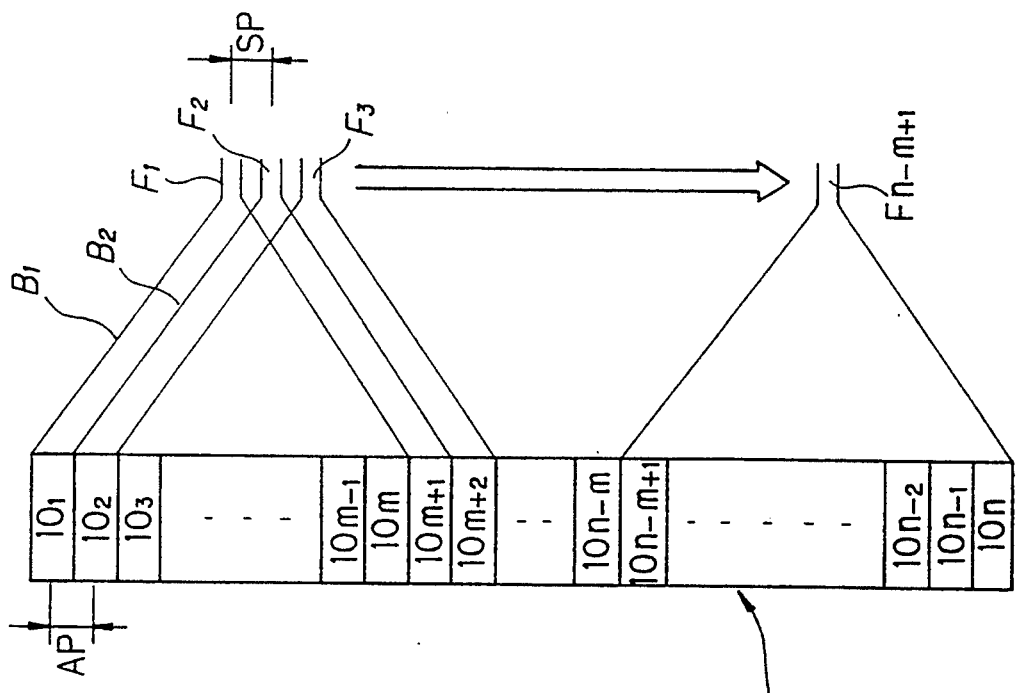
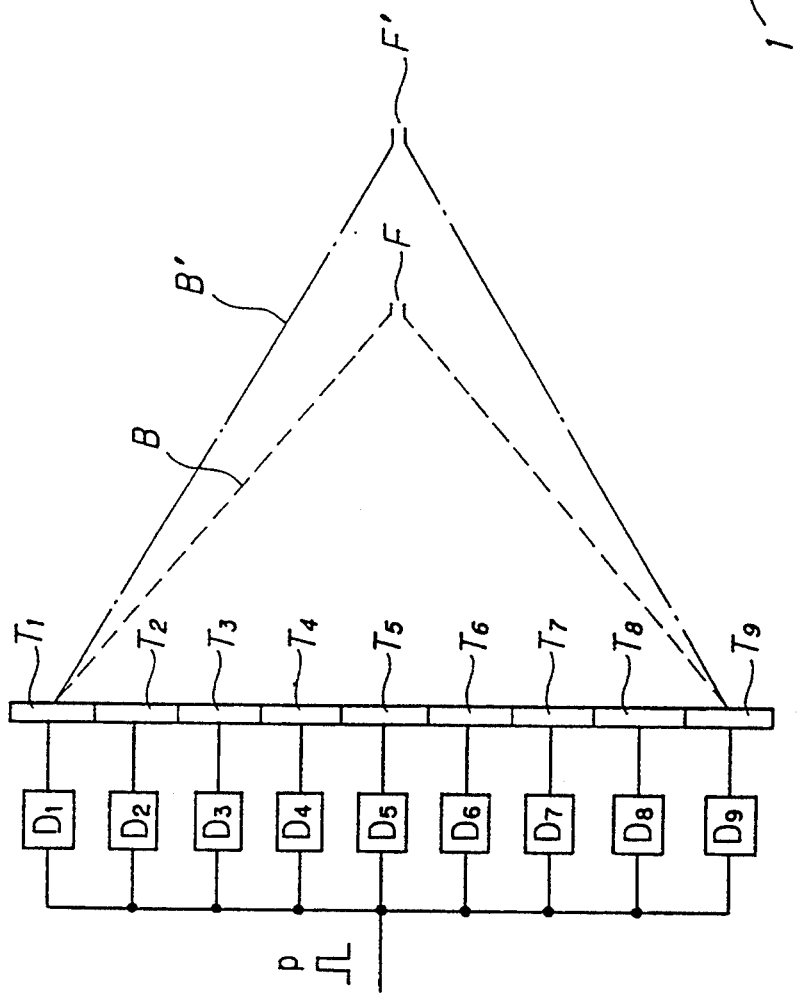

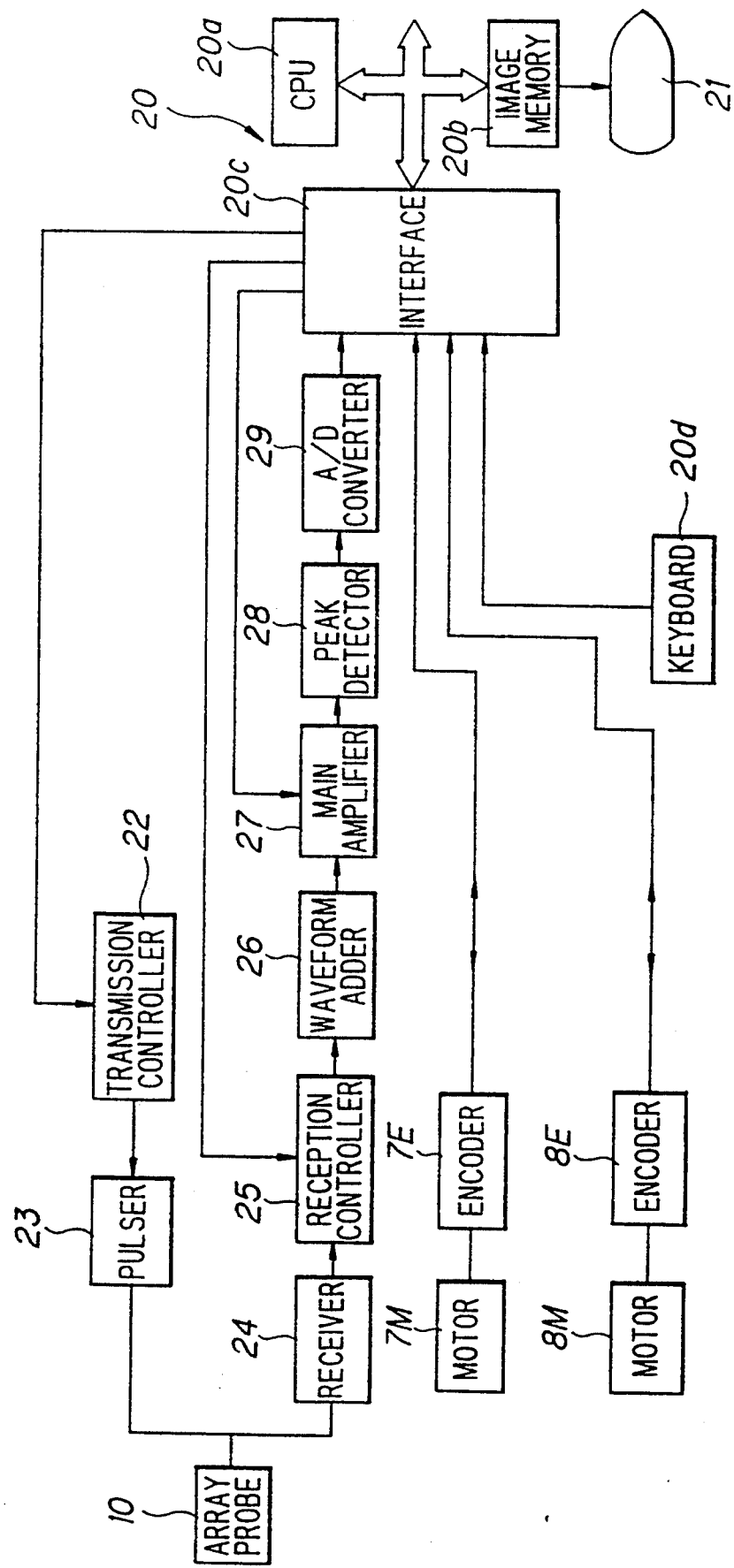

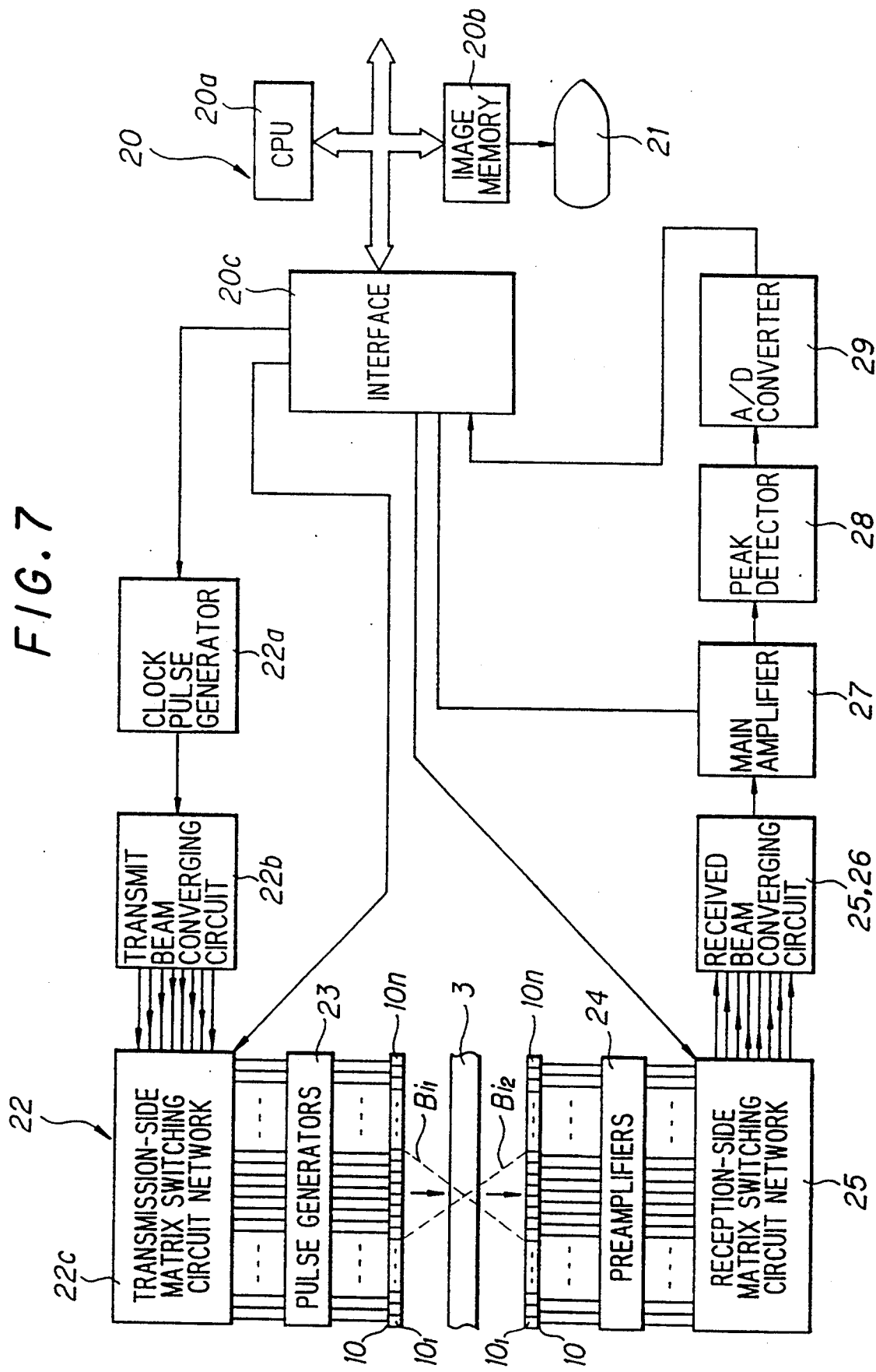

ULTRASONIC INSPECTION SYSTEM

This application is a continuation of International Application PCT/JP90/00754, filed Jun. 8, 1990.

TECHNICAL FIELD

This invention relates to an ultrasonic inspection system, which radiates an ultrasonic wave to an object to scan the same and inspects the surface condition of the object and the existence or absence of any internal defects in the object on the basis of a wave reflected by the object.

BACKGROUND ART

Ultrasonic inspection systems have found widespread utility in a variety of fields as they can detect the internal defects of an object without destruction of the object. The existence or absence of internal defects in an object is often checked over a predetermined range or area of the object. In this case, the predetermined range or area of the object is scanned by an ultrasonic wave radiated from a probe of an ultrasonic inspection system to practice the inspection of the object. As such probes, array probes composed individually of a number of piezoelectric elements arranged in a row have been actually employed. An ultrasonic inspection system making use of such an array probe will hereinafter be described.

FIG. 1 is a perspective view of a scanner unit of the conventional ultrasonic inspection system, while FIG. 2 and FIG. 3 are plan and side views of the array probe, respectively. In each figure of the drawings, there are shown a water tank 1 for conducting an inspection therein, water 2 contained in the water tank 1, and an object 3 placed on a bottom wall of the water tank 1. Designated at numeral 4 is a scanner, which is constructed of the following members: a scanner base 5 with the water tank 1 mounted thereon, frames 6 fixed on the scanner base 5, an arm 7 mounted on the frames 6, a holder 8 placed on the arm 7, a pole 9 attached to the holder 8, and the array probe designated at numeral 10. The frame 6 can drive the arm 7 along Y-axis by an unillustrated mechanism, while the arm 7 can drive the holder 8 along X-axis by a mechanism also not illustrated. Further, the holder 8 can drive the array probe 10 along Z-axis (in a direction perpendicular to X-axis and Y-axis) by a mechanism (not shown) in cooperation with the pole 9.

The array probe 10 is construction of a number of minute piezoelectric elements, which will hereinafter be called "array element oscillators", arranged in a row. The direction of their arrangement is in coincidence with X-axis. Upon application of a pulse, each array element oscillator radiates an ultrasonic wave and converts its reflection wave from the object 3 into a corresponding electrical signal. The individual array element oscillators are indicated at numerals $10_1$–$10_n$ in FIG. 2 and FIG. 3. Incidentally, dots indicate sampling points, YP a sampling pitch along Y-axis, and XP a sampling pitch along X-axis. Further, AP designates the pitch between the individual array oscillators $10_1$–$10_n$. Designated at numeral 11 is a casing which accommodates the array probe 10 and the like.

The function of the array probe 10 shown in each figure described above will now be outlined with reference to FIG. 4 and FIG. 5. In FIG. 4, there are shown array element oscillators $T_1$–$T_9$ arranged in a row, delay elements $D_1$–$D_9$ connected to the array element oscillators $T_1$–$T_9$, respectively, and a pulse p to be inputted to the individual array element oscillators $T_1$–$T_9$. The delay elements $D_1,D_9$ are set to have the same delay time ($t_{19}$). Similarly, the delay elements $D_2,D_8$ are set at the same delay time ($t_{28}$), the delay elements $D_3,D_7$ at the same delay time ($t_{37}$), and the delay elements $D_4,D_6$ at the same delay time ($t_{46}$). The individual delay times so set satisfies the relationship of the following inequality:

$$t_{19} < t_{28} < t_{37} < t_{46} < t_5 \tag{1}$$

where $t_5$ is the delay time of the delay element $D_5$.

Now assume that the pulse p is inputted after setting the delay time of the individual delay elements $D_1$–$D_9$ at predetermined values while maintaining the relationship of the inequality (1). Ultrasonic waves are then radiated from the respective array element oscillators $T_1$–$T_9$ in accordance with the above-set delay times so that the ultrasonic waves from the array element oscillators $T_1,T_9$ are radiated first and the ultrasonic wave from the array element oscillators $T_5$ is radiated last. The ultrasonic waves radiated as described above advance while spreading radially. There is a point where the maximum amplitude of vibrations of the ultrasonic wave from each array element oscillator coincides. This point is indicated by letter F in FIG. 4. Since the magnitude of the ultrasonic wave at this point F is far greater compared to the magnitudes of the ultrasonic wave at other points, a state is developed as if the ultrasonic waves from the individual array element oscillators $T_1$–$T_9$ have converged at the point F as indicated by dashed lines. In other words, if suitable delays are applied to the radiation of ultrasonic waves from the array element oscillators arranged in a row, the ultrasonic waves radiated from the individual array element oscillators can be brought into a state similar to the state that these ultrasonic waves have converged at the point F. This point F is called the "focal point". Describing this further, the ultrasonic beams B which converge at the focal point F as indicated by the dashed lines are outputted by the array element oscillators $T_1$–$T_9$. If the individual delay times are set smaller than their corresponding delay times described above while maintaining the relationship of the formula (1), the focal point F is caused to move to a longer focal point F' as indicated by alternate long and short dash lines (beams B'). It is, therefore, possible to choose the position of the focal point by adjusting the delay times of the delay elements $D_1$–$D_9$. Application of this to the inspection of the object 3 makes it possible to choose the depth of the site to be inspected.

FIG. 5 schematically illustrates the function of the array probe 10 depicted in FIG. 2 and FIG. 3. In this figure, numerals $10_1$–$10_n$ indicate the same array element oscillators as those shown in FIG. 2 and unillustrated delay elements are connected to the respective array element oscillators $10_1$–$10_n$. In the illustrated embodiment, m pieces of the array element oscillators $10_1$–$10_m$ are first selected and the delay times for ultrasonic waves to be radiated from these oscillators are suitably set, whereby the ultrasonic waves apparently converge at a singe focal point as described above. These focal point and apparent ultrasonic beams are indicated by symbols $F_1$ and $B_1$ in FIG. 5, respectively. The array element oscillators with the numbers increased by one are next selected and, to the like number, i.e., m pieces of the array element oscillators $10_2$–$10_{m+1}$, delay times of the same pattern as those applied to the array element oscillators $10_1$–$10_m$ in the preceding delay operation are applied. The resulting focal point is indicated at symbol $F_2$ whereas the ultrasonic beams so radiated are indicated by symbol $B_2$. The array element oscillators with the numbers successively increased one by one are then selected and, at the end, the array element oscillators $10_{n-m+1}$–$10_n$ are selected and the delay times of the same pattern are applied to the array element oscillators $10_{n-m+1}$–$10_n$ to obtain a focal point $F_{n-m+1}$ and ultrasonic beams $B_{n-m+1}$. By the method as described above, the array probe 10 has performed ultrasonic scanning from the focal point $F_1$ to the focal point $F_{n-m+1}$ as a consequence. Since this scanning is performed electronically at a high speed, it will hereinafter be called "electronic scanning". Incidentally, in FIG. 5, "AP" indicates the pitch between array element oscillators while "SP" designates a sampling pitch. In the illustrated embodiment, they are equal to each other.

A description will next be made of a control unit of the ultrasonic inspection system making use of the array probe.

FIG. 6 is a block diagram of the control unit, in which there are illustrated the array probe 10 described above, motors 7M,8M for driving the arm 7 along Y-axis and the holder 8 along X-axis, respectively, and encoders 7E,8E for outputting drive signals to the corresponding motors 7M,8M and detecting and outputting their driven distances. Incidentally, the motor 8M and encoder 8E are used to position the array probe 10 at a suitable location inside the water tank 1 and do not take part in ultrasonic scanning along X-axis, said scanning being to be described later. Designated at numeral 20 is a signal processor, which is composed of a CPU (central processing unit) 20a, an image memory 20b for image processing, an interface 20c for performing input/output operation between the signal processor 20 and external circuits, a keyboard 20d, etc. Although the signal processor 20 is additionally equipped with memory devices such as RAM and ROM, their illustration is omitted. Numeral 21 indicates a display.

Designated at numeral 22 is a transmission controller which, in accordance with commands from CPU 20a, controls the delay times and the selection and changeover of array element oscillators, said delay times, selection and change-over having been described above with reference to FIG. 4 and FIG. 5. There is also illustrated pulsers 23 for outputting a pulse p. These pulsers 23 are provided corresponding to the respective array element oscillators. Numeral 24 indicates receivers for receiving reflected ultrasonic signals from the corresponding array element oscillators and then for amplifying the same. These receivers 24 are also provided corresponding to the respective array element oscillators. Designated at numeral 25 is a reception controller which performs control of the aforementioned delay, selection and change-over for signals from the respective array element oscillators. There is also illustrated a waveform adder 26 for adding all reception signals outputted at the same time as a result of the delays at the reception controller 25. Numeral 27 is a main amplifier for amplifying each output signal from the waveform adder 26. The degree of amplification by the main amplifier 27 is determined by a command from CPU 20a, which command is in turn determined based on an input from external equipment such as the keyboard 20d. Numeral 28 designates a peak detector, which is equipped with the function that only signals within a predetermined depth range are collected and only the peak value among the signals within the range is held and outputted. Designated at numeral 28 is an A/D converter for converting the peak value, which has been held in the peak detector 28, into its corresponding digital value. Operation of the control unit will be described with reference to FIG. 7.

FIG. 7 is a more detailed block diagram of the control unit so that the description of the operation of the control unit shown in FIG. 6 can be facilitated. In FIG. 7, elements either identical or equivalent to those depicted in FIG. 6 are identified by like reference numerals or symbols. Further, illustration of the motors 7M,8M, encoders 7E,8E and keyboard 20d are omitted. In addition, two array probes are shown. This is to mean that the array probe is a separated transmit-receive array probe with one of the array probes 10 being for transmission and the other for reception. Such an array probe is employed with a view toward improving the resolution in the depthwise direction. Incidentally, in the case of a combined transmit-receive array probe of the type that the same array element oscillators are used for both transmission and reception, the construction and operation of the control unit are also the same as in the case of the separated transmit-receive array probe.

FIG. 7 also illustrates a clock pulse generator 22a, a transmit beam converging circuit 22b and a transmission-side matrix switching circuit network 22c. They make up the transmission controller 22 depicted in FIG. 6. Further, a receiving beam converging circuit 25,26 constitutes a part of the reception controller 25 and the waveform adder 26, both depicted in FIG. 6.

Now assume that transmission and reception of a single ultrasonic beam is performed by eight array element oscillators. The transmit beam converging circuit 22b outputs in a predetermined delay pattern signals, which are to be applied to eight pulse generators out of the pulse generators 23, on the basis of a clock pulse from the clock pulse generator 22a. Pursuant to a command from CPU 20a, the transmission-side matrix switching circuit network 22c determines to which array element oscillators, in other words, to which pulse generators the eight signals outputted in the predetermined delay pattern from the transmit beam converging circuit 22b should be applied, and performs switching in accordance with the selection. At the pulse generators 23, signals are outputted in the above-described predetermined delay pattern from the above-selected eight consecutive pulse generators, whereby the array element oscillators connected to these pulse generators, respectively, are excited to output the desired ultrasonic beam.

On the other hand, the array element oscillators on the reception side receive the ultrasonic wave so that signals corresponding to the ultrasonic wave are outputted to the corresponding preamplifiers of the preamplifiers 24, said corresponding preamplifiers being connected to the eight array element oscillators. These signals are therefore amplified. In accordance with a command from CPU 20a, the reception-side matrix switching circuit network 25 feeds the signals, which have been amplified by the respective preamplifiers, one by one to the corresponding ones of the delay elements which are contained in the received beam converging circuit 25,26 and create delay patterns. As a consequence, the eight signals so received are outputted at the same timing in the output stages from the corresponding delay elements of the received beam converging circuit 25,26 and are then added together.

At the main amplifier 27, the signal so added is amplified in accordance with an amplification degree set by a command from CPU 20a. The signal so amplified is delivered through the peak detector 28 and A/D converter 29 so that it is converted to a digital value. The value so converted is then stored at an address of the image memory 20b, said address having been determined as a result of an address arithmetic operation at CPU 20a.

The operation of transmission and reception of a single ultrasonic beam by eight array element oscillators has been described above. By suitably switching and controlling the transmission-side matrix switching circuit network 22c and the reception-side matrix switching circuit network 25, the individual array element oscillators $10_1$–$10_n$ of the array probe 10 can be selected in groups, each consisting of eight array element oscillators, while successively increasing the numbers of the eight array element oscillators one by one. As a consequence, electronic scanning along X-axis can be carried out. Upon completion of the electronic scanning, the motor 7M is driven in accordance with a command from CPU 20a so that the arm 7, namely, the array probe 10 is shifted by the predetermined sampling pitch YP along Y-axis (mechanical scanning). In this state, electronic scanning of a second row, as viewed along X-axis, by ultrasonic wave is performed in a manner similar to the electronic scanning described above. By repeating such an operation, ultrasonic scanning of the X-Y plane of the object 3 can be performed. During the ultrasonic scanning, signals of reflected waves received at the individual receivers 24 are successively stored at prescribed addresses, respectively, in the image memory 20b. Based on the data stored in the image memory 20b, an ultrasonic image of the object 3 by the above ultrasonic scanning is shown on the display 21. Checking of any defects in the object 3 can be conducted by observing the ultrasonic image so displayed.

The scanning time in each single line along X-axis is extremely short so that the mechanical scanning along Y-axis can be performed without interruption in the course of the inspection. Further, the number of array element oscillators in each group to be selected can be set as desired.

More detailed construction of the transmit beam converging circuit 22b, transmission-side matrix switching circuit network 22c, pulse generators 23, preamplifiers 24, reception matrix switching circuit network 25 and received beam converging circuit 25,26, all illustrated in FIG. 7, are disclosed in Japanese Patent Application Laid-Open (Kokai) No. HEI 2-69654.

The conventional ultrasonic inspection system described above can promptly and accurately inspect the existence or absence of defects in the object 3. It is, however, to be noted that the signal level may scatter from one data sampling to another when the data sampling is conducted at individual focal points in electronic scanning (i.e., scanning along X-axis) by the above-described conventional ultrasonic inspection system. This is shown in FIG. 8, in which sampling points in the direction of electronic scanning are plotted along the axis of abscissas while the levels of received signals are plotted along the axis of ordinates. As is clearly envisaged from the figure, the levels of received signals scatter to a substantial extent. The present inventors conducted an investigation to determine possible causes for the occurrence of such scattering. As a result, it has been found that its primary cause resides in the array probe 10, pulser 23 and receiver 24. This will next be described with reference to drawings.

FIG. 9 is a detailed block diagram of the array probe, pulser and receiver, in which numerals $10_1$–$10_n$ indicate the individual array element oscillators constituting the array probe 10. As has been described above, the individual array element oscillators $10_1$–$10_n$ are connected to corresponding pulsers $23_1$–$23_n$ and receivers $24_1$–$24_n$. Each single channel for transmitting and receiving a single ultrasonic beam is constructed by the combination of one of the array element oscillators, its corresponding pulser and receiver, and plural conductors connecting them. In such a construction, the existence of certain differences in sensitivity among the individual array element oscillators $10_1$–$10_n$, pulsers $23_1$–$23_n$ and receivers $24_1$–$24_n$ cannot be avoided. If an array element oscillator, a pulser and a receiver, all having low sensitivity, are connected, the level of a signal to be received through the resulting channel will be appreciably reduced. If an array element oscillator, a pulser and a receiver, all having high sensitivity, are connected conversely, the level of a signal to be received through the resulting channel will be appreciably higher. As a result, the levels of signals received through the individual channels scatter.

FIG. 10 illustrates inspection of a defect-containing object by an ultrasonic inspection system with such scattering in received signals as described above, while FIG. 11 shows an ultrasonic image obtained as a result of the inspection depicted in FIG. 10. FIG. 10 shows the object 3, a concaved defective portion 3f of the object 3, and the array probe 10. On the other hand, FIG. 11 illustrates a screen 21a of the display 21, an ultrasonic image A of the contour of the object 3, and an ultrasonic image 3f' of the defective portion 3f. Symbols $G_1$–$G_6$ indicate stripes occurring along Y-axis as a result of the scattering of signals received through the individual channels in the ultrasonic inspection system (in practice, a number of stripes of various widths occur). Upon observation of the ultrasonic image, these stripes make it difficult to watch the overall image and, hence, to discover the defective portion. Where the difference in level between ultrasonic signals from the defective portion and those from a defect-free portion is very small, for example, inconvenience is caused because their boundary becomes unclear due to interference by the stripes.

As a method for eliminating such scattering, one could consider providing the individual pulsers $23_1$–$23_n$ or receivers $24_1$–$24_n$ with sensitivity adjusters, respectively, so that the levels of received signals can be controlled. This method may be feasible where the total number n of the array element oscillators is small. Where the total number n ranges from 100 to 200, an extremely long time is required for the sensitivity adjustment alone and, in addition, any attempt to automate the sensitivity adjustment for shortening the time required therefor leads to the need for an enormous circuit-loading area and their control becomes extremely complex. Moreover, even if such sensitivity adjusters are provided, the entire sensitivity adjustment must be conducted again when the array probe is replaced (such a replacement is done frequently). In addition, the following problem still exists even if the above sensitivity adjusters are provided. Namely, the cause for scattering in sensitivity also exists in the reception controller 25 provided next to the receiver 24. Since the reception controller 25 has plural input/output signal lines, the intensity of an ultrasonic signal varies depending on which one of the signal lines the ultrasonic signal passes through. Because of this, even if scattering in sensitivity at the stage of the pulsers or receivers is eliminated completely, scattering still occurs as a result of the passage of signals through subsequent signal lines.

An object of this invention is overcome the above problems of the conventional art and, hence, to provide an ultrasonic inspection system which can easily eliminate the influence of the scattering of received signals and can display a clear image of a defective portion to permit accurate inspection of an object.

DISCLOSURE OF THE INVENTION

In an ultrasonic inspection system equipped with an array probe composed of a number of array element oscillators arranged in at least one row, a memory unit for storing ultrasonic data obtained by ultrasonic scanning of a surface of an object by the array probe, and a display unit for showing an ultrasonic image based on the data stored in the memory unit, the present invention, in one aspect, first conducts ultrasonic scanning of a reference material of defect-free uniform quality, for example, a bottom wall or the like of a water tank, in which the object is to be placed, thereby collecting reference data, and an average value of the data is computed by a first computing means. When the object has been ultrasonically scanned, various inspection data obtained by the ultrasonic scanning, the average value and the inverses of the reference data collected through the same channels as those employed to sample the various inspection data are then multiplied by a second computing means. By this multiplication, corrected inspection data available when the individual elements have the same sensitivity are obtained. These corrected inspection data are outputted to the display unit so that a clear ultrasonic image can be obtained.

According to another aspect of this invention, similarly to the aspect described above, a reference material of defect-free uniform quality such as a bottom wall of a water tank is first subjected to ultrasonic scanning to collect reference data. Based on the ratios of the reference data in each sampling by the ultrasonic scanning to a minimum value of the reference data collected or a predetermined constant value not greater than the minimum value, attenuation ratios are computed by a computing means in advance. When the object has been ultrasonically scanned, various inspection data obtained by the ultrasonic scanning are corrected by a correction means on the basis of the attenuation factors for the corresponding channels. These corrected inspection data are shown on the display unit, whereby a clear ultrasonic image can be obtained.

BRIEF DESCRIPTION OF THE DRAWINGS

FIGS. 4 and 5 are schematic illustrations of the function of the array probe, FIG. 6 is a block diagram of a conventional ultrasonic inspection system, FIG. 7 is a more detailed block diagram of the system of FIG. 6.

BEST MODES FOR CARRYING OUT THE INVENTION

The present invention will be described in further detail with reference to some of the accompanying drawings.

Figure 12:
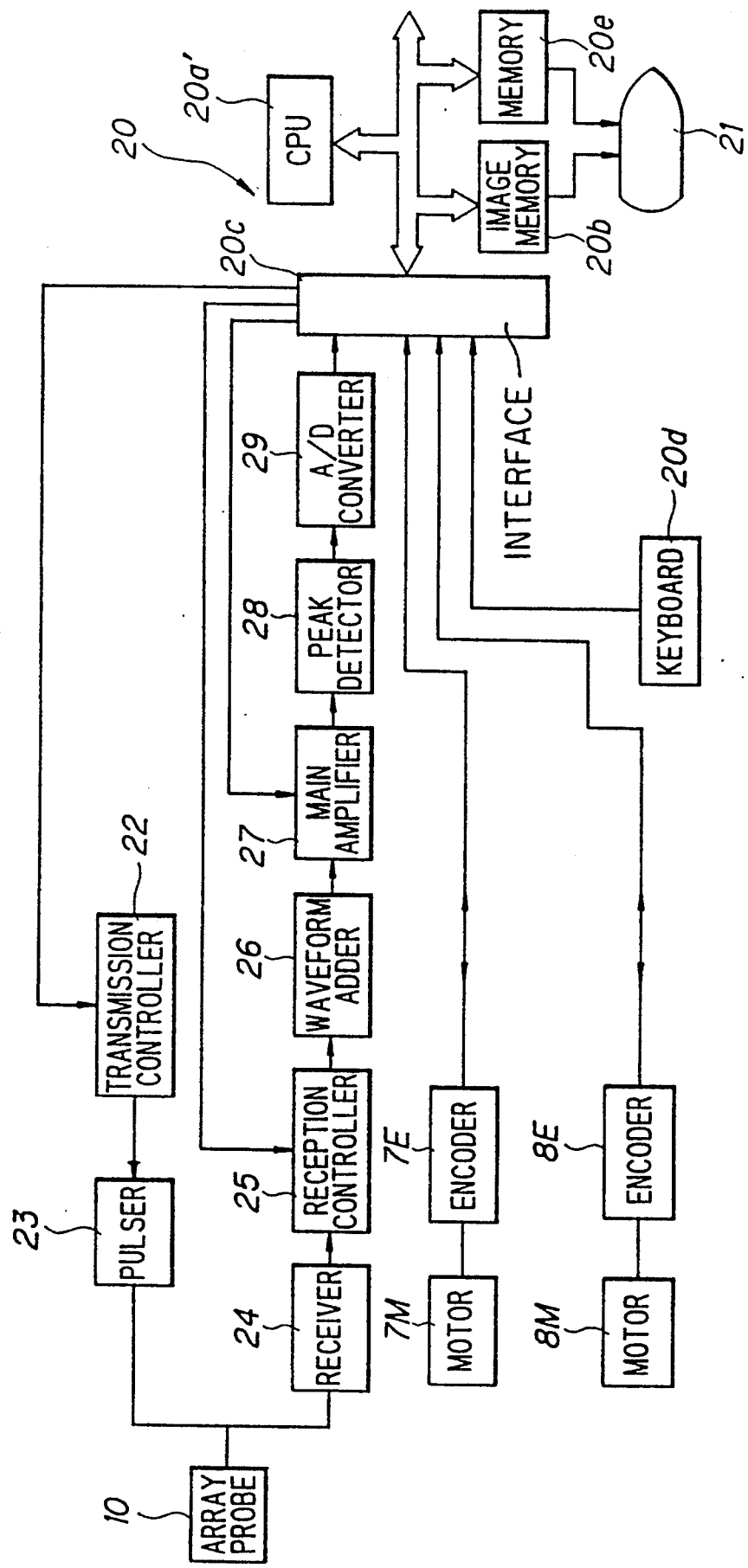
FIG. 12 is a block diagram of an ultrasonic inspection system according to a first embodiment of this invention.

FIG. 12 is a block diagram of an ultrasonic inspection system according to a first embodiment of this invention. In the drawing, elements either identical or equivalent to those shown in FIGS. 6 or 7 are identified by like reference numerals or symbols and their description is omitted. Numeral $20a'$ indicates a CPU equivalent to CPU $20a$. CPU $20a'$ is different in processing procedures from CPU $20a$. Designated at numeral $20e$ is a memory provided in addition to the image memory $20b$.

Figure 1:
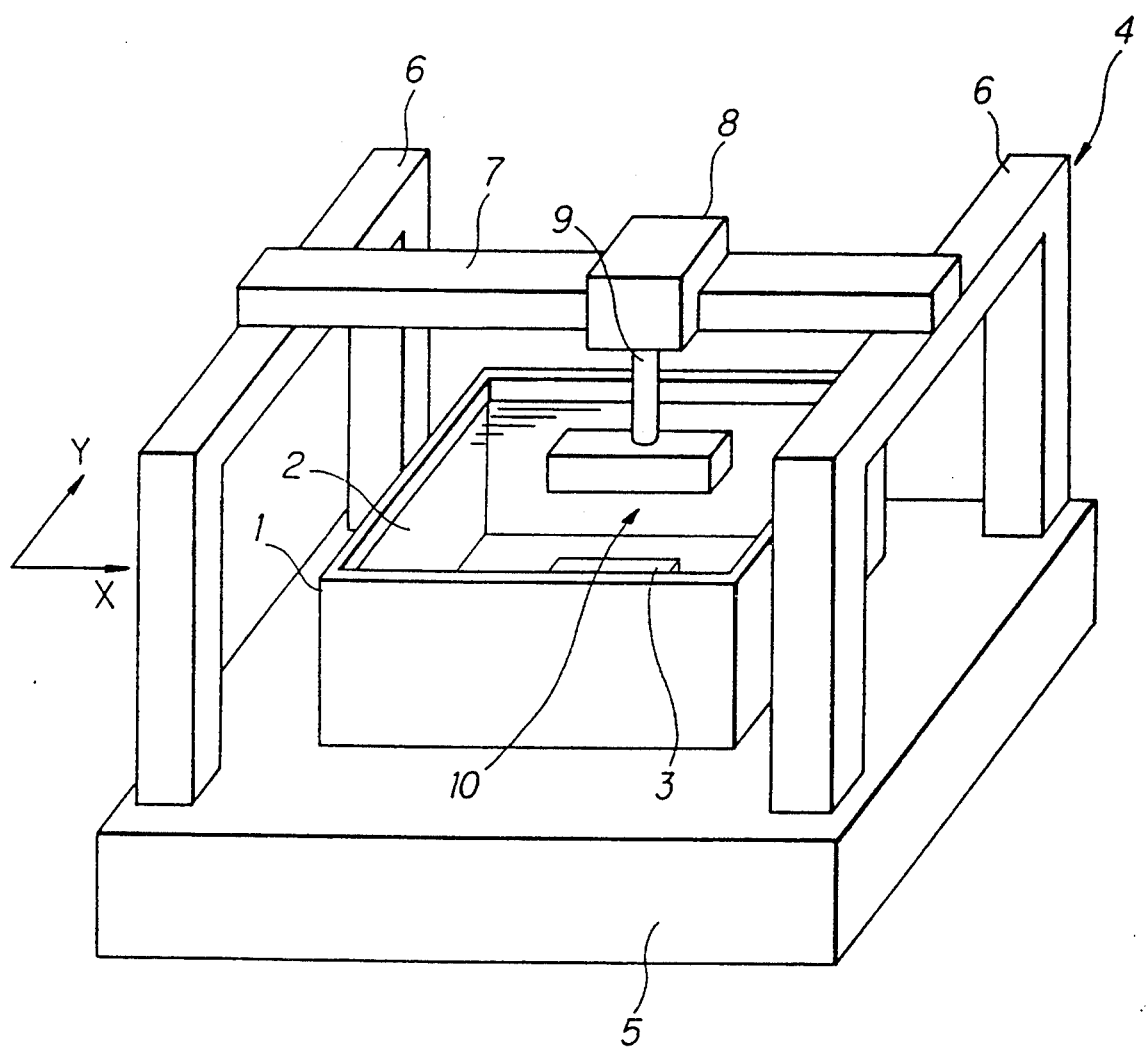
FIG. 1 is a perspective view of a scanner unit of an ultrasonic inspection system.
Figure 2:
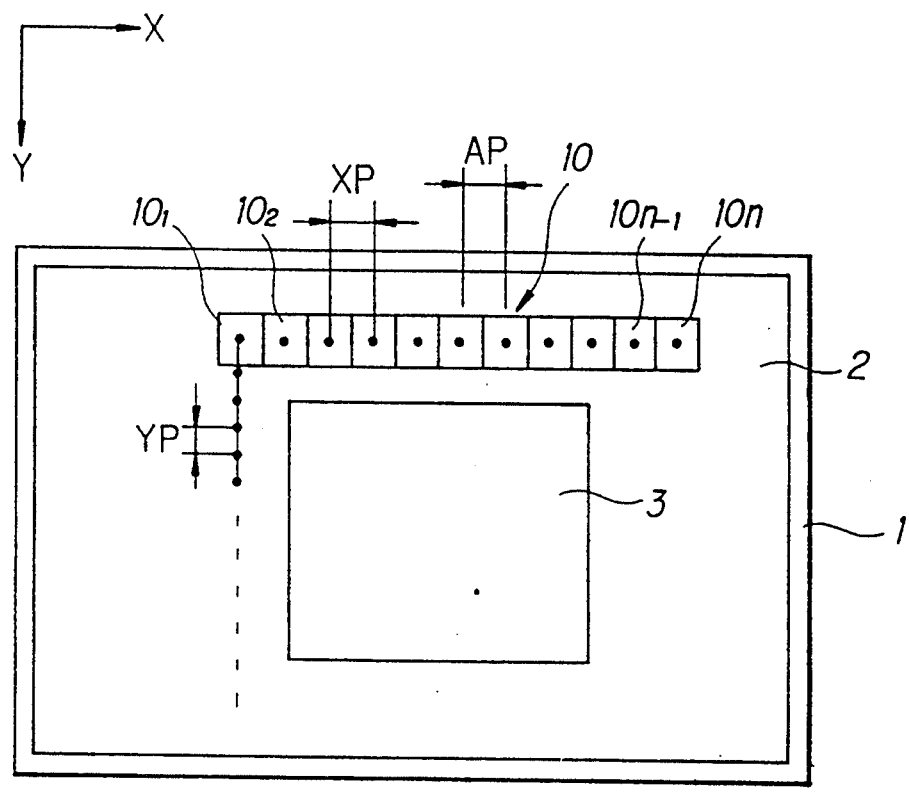
FIGS. 2 and 3 are plan and side views of an array probe.
Figure 3:
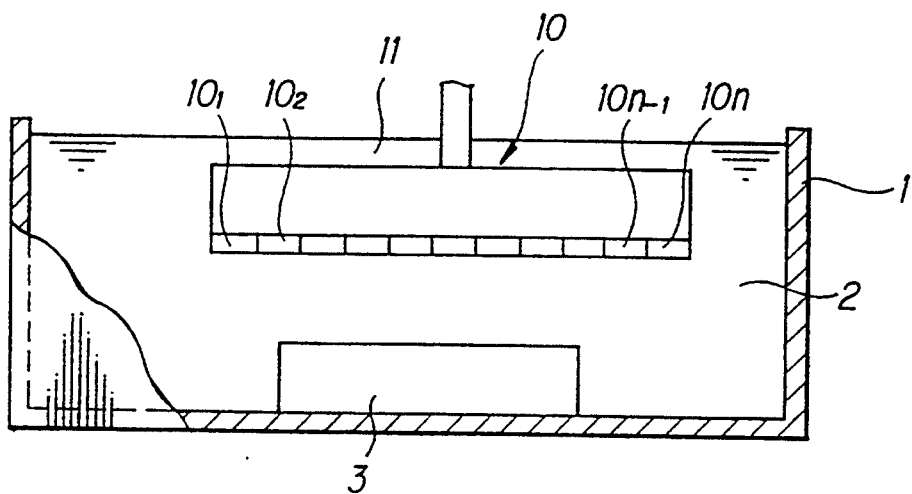
Figure 8:
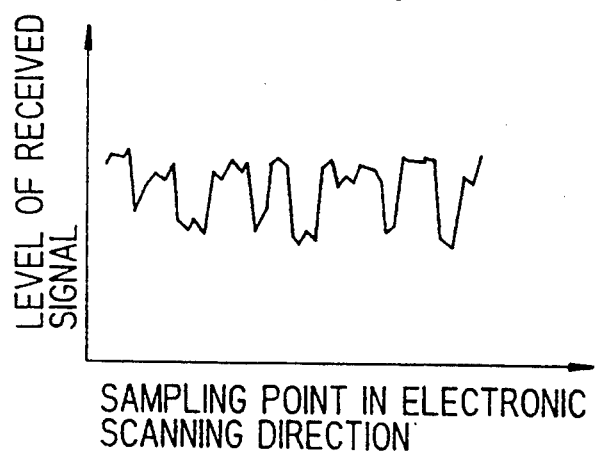
FIG. 8 is a waveform diagram of received signals.
Figure 9:
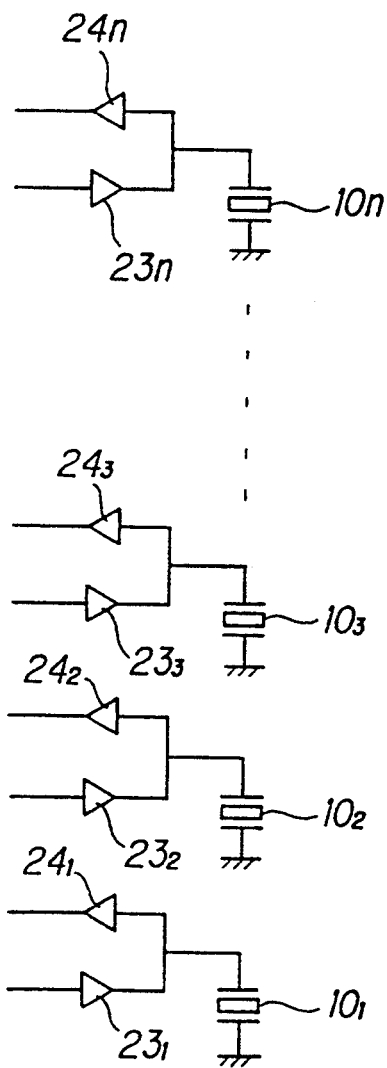
FIG. 9 is a detailed block diagram of individual array probes, pulsers and receivers.
Figure 10:
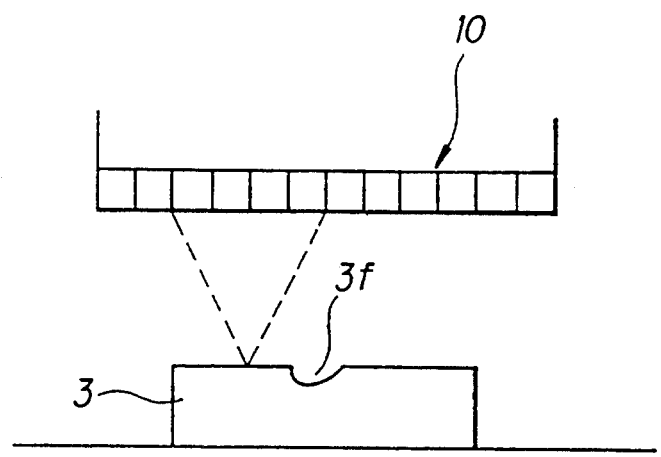
FIG. 10 is a side view of an object having a defective portion.
Figure 13:
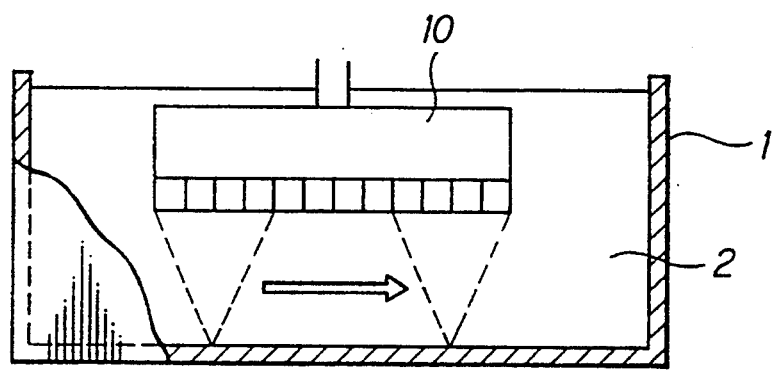
FIG. 13 is a cross-sectional view of a water tank.
Figure 14:
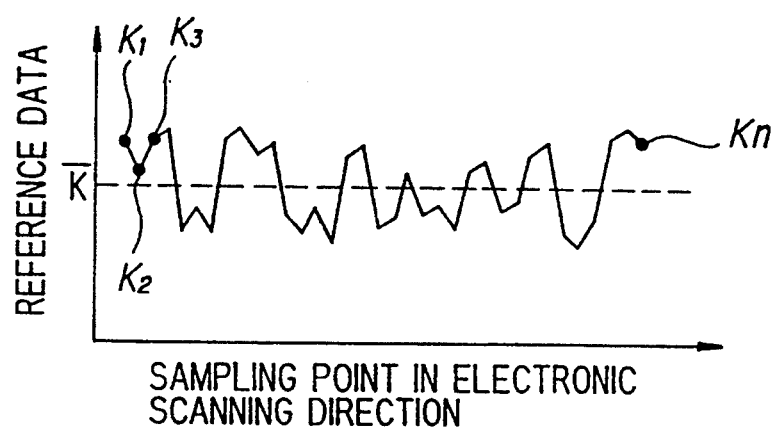
FIG. 14 is a graph of reference data.

The operation of this embodiment will next be described with reference to FIG. 13 and FIG. 14. FIG. 13 is a cross-sectional view of a water tank with an array probe inserted therein. There are shown the water tank at numeral 1, water 2 placed in the water tank 1, and the array probe identified at numeral 10. These water tank and array probe are the same as those illustrated in FIGS. 1, 2 and 3. In the present embodiment, prescribed procedures (preparation work) are conducted prior to each ultrasonic inspection. This preparation work will hereinafter be described.

First, CPU $20a'$ conducts, by the array probe 10, ultrasonic scanning with respect to the bottom wall (formed flat with an acrylic material) of the water tank 1, on which the object 3 is not placed, along one line as indicated by an arrow in FIG. 13 in the same manner as in the ultrasonic inspection of the object 3, whereby data which are A/D-converted data and will be called "reference data" are collected and stored in a suitable memory of the signal processor 20. FIG. 14 is a graph of these reference data, in which sampling points in the electronic scanning direction are plotted along the axis of abscissas while reference data are plotted along the axis of ordinates. $K_1, K_2, K_3, \ldots K_n$ designate individual reference data. The graph has been prepared by successively connecting these reference data with a straight line. As is evident from the graph, these reference data do not have the same value despite they were obtained by the ultrasonic scanning of the bottom wall (reference material) of the water tank 1, said bottom wall having been formed smooth with the same material, but include scattering due to the above-described differences in sensitivity. CPU 20a' computes an average value $\overline{K}$ of these reference data (n pieces of data) in accordance with the following formula (1) and stores it.

$$\overline{K} = \frac{1}{n} \sum_{i=1}^{n} K_i \quad (2)$$

The average value $\overline{K}$ can be considered as data available when the bottom wall of the water tank 1 is ultrasonically scanned at the average sensitivity of all the sensitivities.

With respect to each of the reference data $K_1, K_2, K_3, \ldots K_n$, CPU 20a' next computes the ratio of the average value $\overline{K}$ to the reference datum $(\overline{K}/K_i)$ and stores the value of the ratio in the memory 20e. The value of the ratio is the inverse of the magnitude of each reference datum $K_i$ to the average value $\overline{K}$ of the respective reference data, in other words, the inverse of the magnitude of sensitivity of each channel, which was employed to collect the datum at the corresponding sampling point on the single electronic scanning line in the ultrasonic scanning, relative to the average sensitivity of the individual channels. The preparation work prior to an ultrasonic inspection has now been completed.

Evidently, the value of each ratio $(\overline{K}/K_i)$ does not vary and always remains constant even if the degree of amplification by the main amplifier 27 changes after the completion of the preparation work.

To conduct an ultrasonic inspection for the object 3, the collection of inspection datum at each sampling point is performed in the same manner as in the conventional system. The inspection data so collected are stored in the image memory 20b. Here, assume that data collected through the individual channels by electronic scanning of a single line out of these inspection data be identified by $Q_1, Q_2, Q_3, \ldots Q_i, \ldots Q_n$, respectively. CPU 20a' multiplies each of these inspection data $Q_1$-$Q_n$ by the value of the ratio $(\overline{K}/K_i)$ of the corresponding channel, said value having been stored in the memory 20e, in accordance with the following formula (3):

$$Q_i' = Q_i \cdot \frac{\overline{K}}{K_i} \quad (i = 1 \text{ to } n) \quad (3)$$

Since the value $Q_i'$ obtained in accordance with the formula (3) is the value obtained by multiplying the inspection datum $Q_i$ with the inverse of the sensitivity at the time of collection of the reference datum through the corresponding channel, the value $Q_i'$ becomes a value equivalent to the inspection datum collected at the average sensitivity. The data $Q_i'$ corrected by the formula (3) as described above are successively replaced whenever the computation of the inspection data $Q_i$ in the image memory 20b by the formula (3) is completed. Incidentally, the computation by the formula (3) can be performed during the time intervals of sampling at the time of electronic scanning or after the sampling along one electronic scanning line has been completed. It can also be performed after all inspection data have been sampled. When the computation by the formula (3) is performed during the intervals of sampling at the time of electronic scanning out of these choices, it is unnecessary to store the inspection data $Q_i$ in the image memory 20b beforehand. It is only required to perform the computation by the formula (3) and to store the result $Q_i'$ of the computation in the image memory 20b when the inspection data $Q_i$ have been obtained. The processing time can be shortened in this manner. In the manner described above, all the corrected data are eventually stored in the image memory 20b.

Where the object 3 is, for example, free of any defects, all the data of the image memory 20b become equal to the average value of the whole inspection data. Where there is a defect, the data of portions other than the defective portion are equal to the average value and only the datum corresponding to the defective portion takes a value different from the average value. When an image is shown on the display on the basis of the data corrected above, any defective portion is displayed in a form clearly distinguished from the other portions where the object 3 contains the defective portion.

Figure 11:
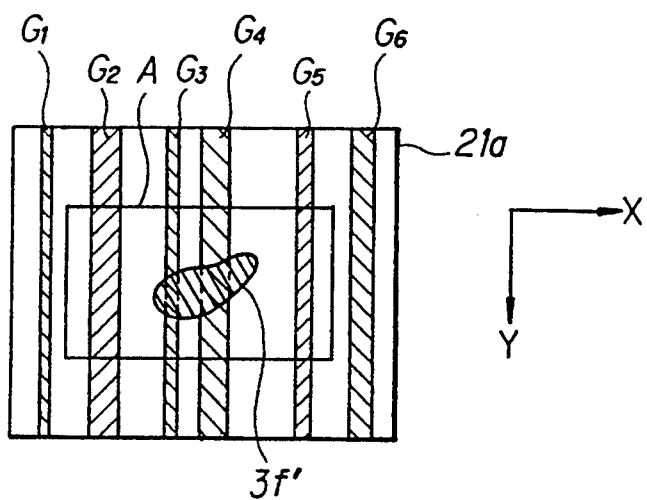
FIG. 11 is a diagram showing an ultrasonic image of the object.

As has been described above, according to this embodiment, the values of ratios $(\overline{K}/K_i)$ of the average value $\overline{K}$ of data $K_i$, which have been collected by ultrasonic scanning of a reference material, to the individual data $K_i$ are obtained beforehand with respect to individual channels and, at the time of an ultrasonic inspection, inspection data collected through the individual channels are multiplied by the values of the ratios of the corresponding channels so that corrected data are obtained. Even if the sensitivity is scattered among the individual channels upon collection of data, stripes such as those shown in FIG. 11 do not appear so that the discovery of a defective portion can be facilitated and the defective portion can be displayed in a form clearly distinguished from the other portions.

As a method for correcting such sensitivity scattering as that described above, one could consider providing a reference material made of the same material as the object and containing no defect and subtracting ultrasonically scanned data (reference data) of the reference material from inspection data of the object. This method, however, requires the storage of reference data at all sampling points, leading to the problem that the capacity of the memory must be large. This method may be effective when many objects of the same configuration are inspected. However, when setting conditions such as the thickness of an object, the points of inspection on the object and the gains of receivers change, the reference data must be changed in accordance with the changes whenever these changes are made. As a consequence, lots of labor and time are required for their modifications. In contrast, this embodiment requires reference data as small as those collected by sampling along one electronic scanning line so that a small memory capacity can be successfully employed. Further, even when conditions on the side of the object or the inspection system vary, there is no need to modify the reference data so that, compared to the method described above, the efficiency of inspection can be improved significantly.

The above embodiment was described using the bottom wall of the water tank as a reference material by way of example. The above embodiment is, however, not limited to its use. Any material can be used as long as its quality is uniform. Further, the description was made of the example that the values of ratios were stored in the memory 20e. Instead, reference values and their average value can be stored. In this case, the computation of corrected data requires to take three data, i.e., the inspection data, the reference data and the average value and then to conduct computation thereon.

Such computing processing can, however, be conducted sufficiently within the time intervals of the sampling. This embodiment was described using, by way of example, the memory 20e for the storage of the values of the ratios. The memory 20e can, however, be obviated provided that the image memory 20b has a space sufficient for their storage. Further, an array probe constructed of array element oscillators arranged in a matrix can also be used as the array probe. In this case, the number of reference data will be equal to the number of all the channels for the ultrasonic beams.

Figure 15:
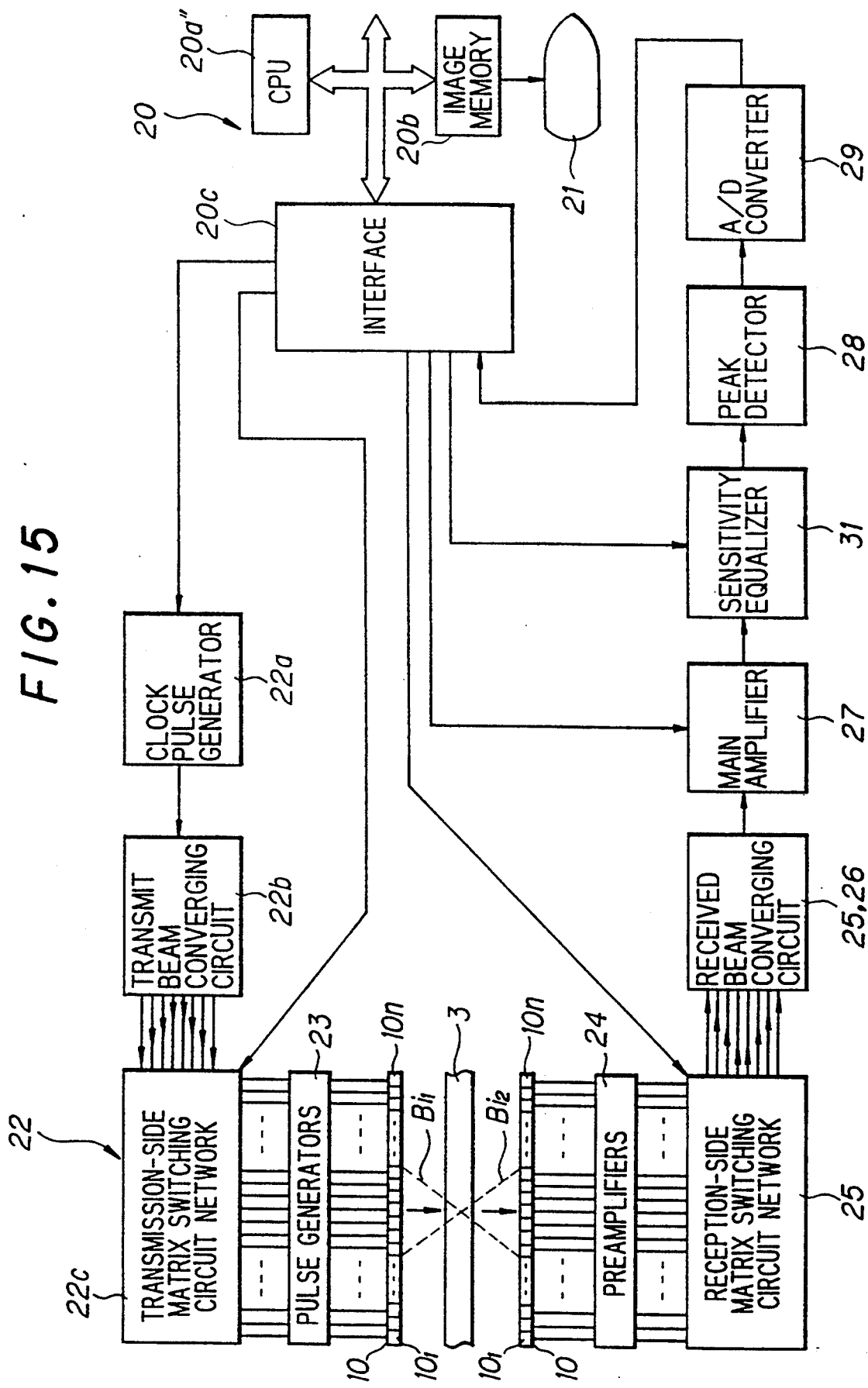
FIG. 15 is a block diagram of an ultrasonic inspection system according to a second embodiment of this invention.

FIG. 15 is a block diagram of an ultrasonic inspection system according to a second embodiment of the present invention. In the figure, elements identical or equivalent to those shown in FIG. 6 or FIG. 7 are identified by like reference numerals or symbols and their description is omitted. Designated at numeral 31 is a sensitivity equalizer interposed between the main amplifier 27 and the peak detector 28. Numeral 20a" indicates a CPU which is also equipped, in addition to the function of the conventional CPU 20a, with function to produce signals to be fed to the equalizer 31.

Figure 16:
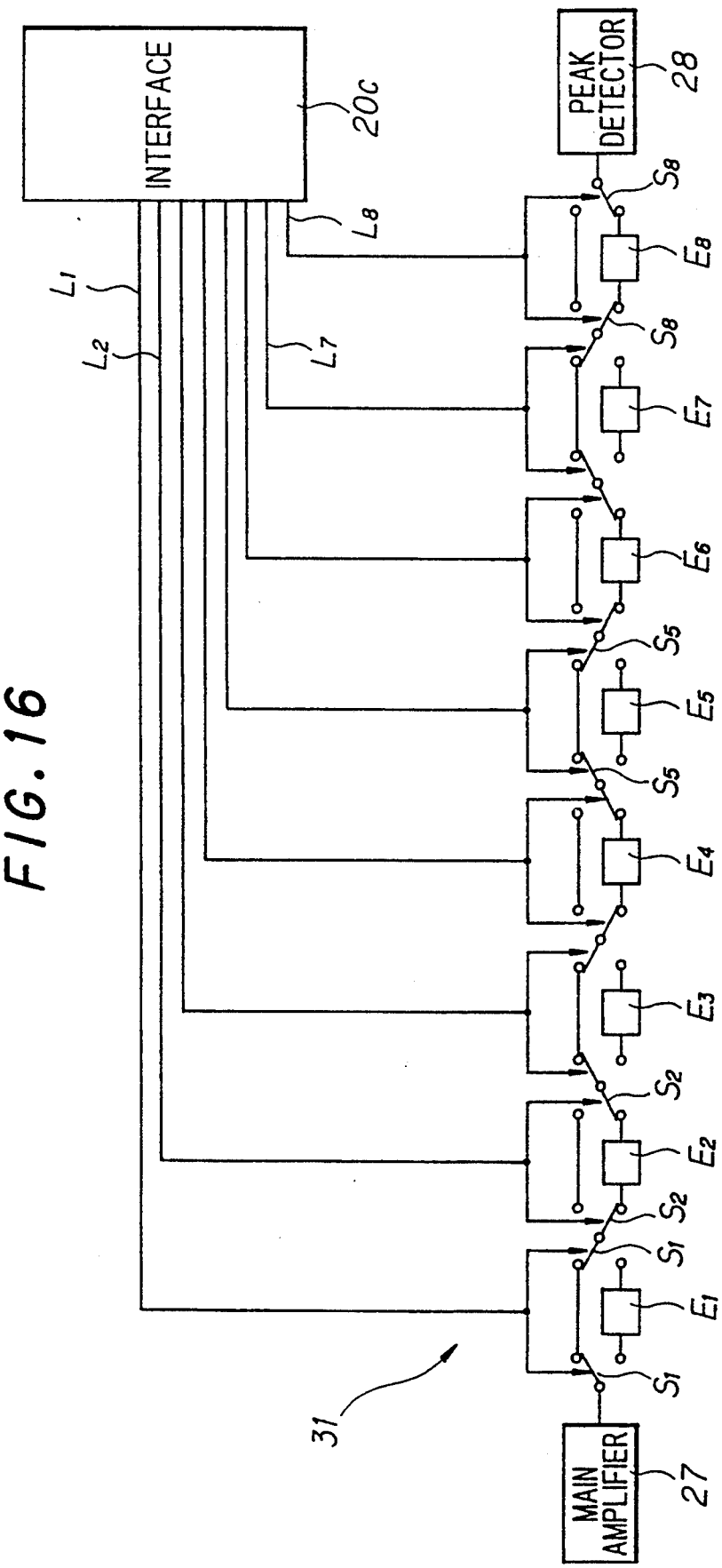
FIG. 16 is a block diagram of a first specific example of a sensitivity equalizer shown in FIG. 15.

FIG. 16 is a block diagram of a first specific example of the sensitivity equalizer 31 shown in FIG. 15. In the figure, symbols $E_1$-$E_8$ indicate signal attenuators. The attenuation factors of the individual signal attenuators $E_1$-$E_8$ can be chosen, for example, as follows: $E_1 = -8$ dB, $E_2 = -4$ dB, $E_3 = -2$ dB, $E_4 = -1$ dB, $E_5 = -0.8$ dB, $E_b = -0.4$ dB, $E_7 = -2$ dB, and $E_8 = -0.1$ dB. Designated at symbols $S_1$-$S_8$ are electronic switching elements provided on the input sides and output sides of the respective signal attenuators $E_1$-$E_8$. It is to be noted that these switching elements are shown as mechanical switches in the figure to facilitate their understanding. Symbols $L_1$-$L_8$ are signal lines connecting the interface 20c to the individual switching elements. Transmitted through these signal lines are digital signals ("1" or "0") for the control of the corresponding switching elements. In this specific example, each of the switching elements $S_1$-$S_8$ is changed over to the position at which the corresponding attenuator is cut off (the upper position in the figure) when the signal "0" is outputted to the corresponding signal line. When the signal "1" is outputted to each signal line on the other hand, the corresponding one of the switching element $S_1$-$S_8$ is changed over to the position where the corresponding attenuator is connected to the interface.

Figure 17:
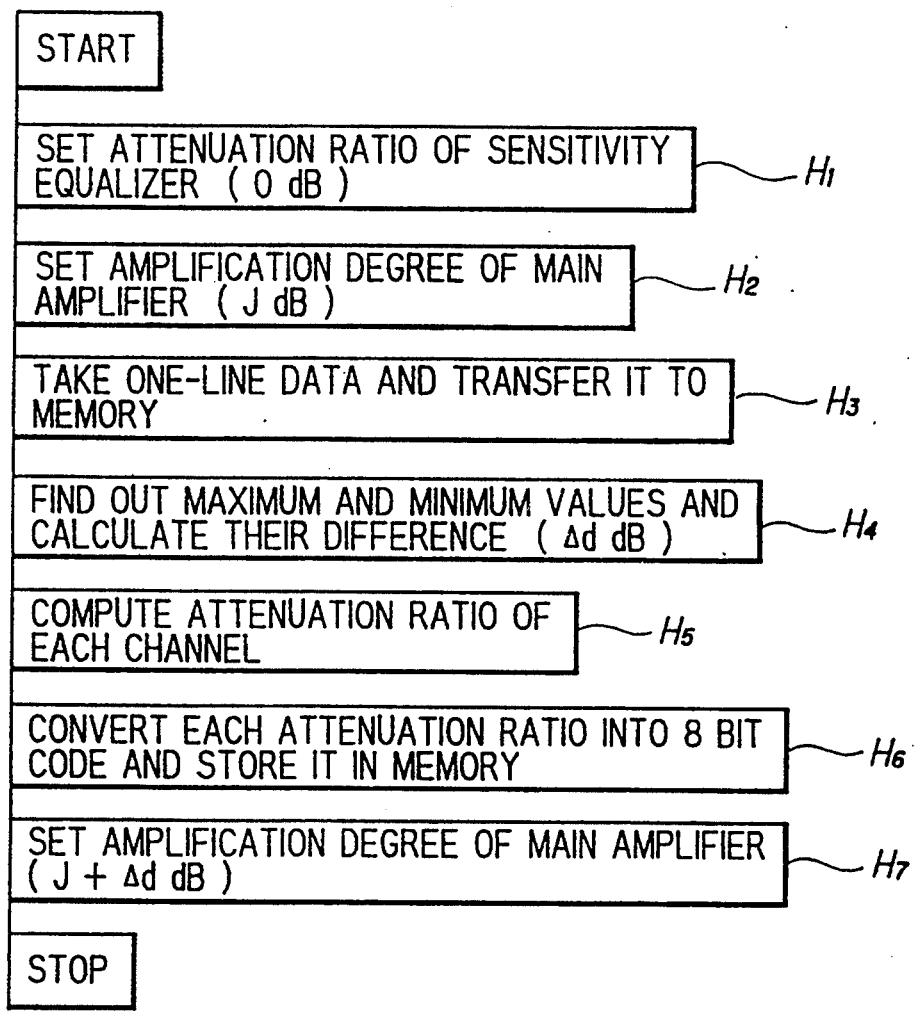
FIG. 17 is a flow chart describing the operation of the system depicted in FIG. 15.

The operation of this embodiment will next be described with reference to the flow chart shown in FIG. 17. Preparation work is also conducted prior to performing an ultrasonic inspection on an object. This preparation work is shown in the flow chart. First, CPU 20a" brings all signals of the signal lines $L_1$-$L_8$ to "0" whereby the switching elements $S_1$-$S_8$ of the sensitivity equalizer 31 are all changed over to the upper sides to allow a signal, which has been outputted from the main amplifier 27, to bypass all the signal attenuators $E_1$-$E_8$. Namely, the attenuation factor of the sensitivity equalizer 31 is set at 0 dB (Procedure $H_1$ in FIG. 17). The degree of amplification by the main amplifier 27 is next set at a suitable value (J dB) (Procedure $H_2$). The ultrasonic inspection system is operated in this state to conduct electronic scanning along one line while using the bottom wall of the water tank 1 as a reference material. The resulting data are transferred to and stored in a suitable memory, for example, inside the signal processor (Procedure $H_3$).

CPU 20a" finds out a maximum value ($K_{max}$) and a minimum value ($K_{min}$) from the data so stored and computes their difference $\Delta d$ in accordance with the following formula (Procedure $H_4$).

$$\Delta d(\text{dB}) = 20\log \frac{K_{max}}{K_{min}} \quad (4)$$

To bring the sensitivities of the individual channels into conformity, the attenuation factor of each channel is next computed (Procedure $H_5$). In this embodiment, using the minimum value $K_{min}$ out of the data collected by the processing of Procedure $H_3$, calculation is performed in accordance with the following formula to determine how much the data of the individual channels, said data being to be represented by values $K_i$, have to be attenuated, in other words, the attenuation factors $G_i$ of the individual channels in order to bring the data $K_i$ of the individual channels to the minimum value $K_{min}$.

$$G_i(\text{dB}) = 20\log \frac{K_i}{K_{min}} \quad (5)$$

The attenuation factors $G_i$ of the individual channels, which have been obtained in accordance with the formula (5), are converted into 8-bit codes on the basis of the attenuation factors set for the signal attenuators $E_1$-$E_8$, respectively, and are stored in the memory of the signal processor 20 (Procedure $H_6$). The above 8-bit codes are determined in the following manner. When the attenuation factor $G_i$ of one of the channels is, for example, 5.5 (dB), $$5.5 = 4 + 1 + 0.4 + 0.1 \quad (6)$$

It is, therefore, only necessary to use the attenuators $E_2, E_4, E_6, E_8$—whose attenuation factors have been set at values equal to the values on the right side of the formula (6), respectively—and not use the other attenuators $E_1, E_3, E_5, E_7$. For this purpose, it is necessary to set the output signals of the signal lines $L_2, L_4, L_6, L_8$ at "1" and those of the signal lines $L_1, L_3, L_5, L_7$ at "0". The 8-bit code can, therefore, be written as "01010101". When expressed by the decimal system instead of the binary system, the above code can be rewritten to "85". When expressed by the hexadecimal system, it can then be rewritten to "55". Such codes of the individual channels are stored in the memory. These codes may be stored in the memory, in which the data obtained by the processing of Procedure $H_3$ are stored, by replacing the data or may be stored at another place.

Finally, the degree of amplification of the main amplifier 27 is reset (Procedure $H_7$). This setting can be conducted by adding the value $\Delta d$, which has been computed in accordance with the formula (4), to the previously-set amplification degree J pursuant to a command from CPU 20a". By this processing of Procedure $H_7$, the preparation work for the ultrasonic inspection on the object has been completed.

When the ultrasonic inspection of the object is performed, CPU 20a" outputs the attenuation factors of the respective channels, said attenuation factors having been stored in the memory, to the corresponding signal lines $L_1$-$L_8$ upon collection of data through the individual channels so that the corresponding switching elements $S_1$-$S_8$ are changed over to set the respective attenuation factors of the sensitivity equalizer 31 at the attenuation factors of the respective channels. The data of the individual channels, which have passed through the sensitivity equalizer with the attenuation factors set as described above, are data which are free of the differences in sensitivity among the individual channels.

A description is now made of reasons for which the signal attenuators $E_1$-$E_8$ are employed as the sensitivity equalizer 31. The sensitivity equalizer 31 is provided to bring the sensitivities of the individual channels into conformity. From this point of view, it is possible to use the maximum value $K_{max}$ as a reference instead of employing the minimum value $K_{min}$ as a reference unlike the above embodiment and, correspondingly, to use plural signal amplifiers in place of the respective signal attenuators $E_1$-$E_8$. It is, however, to be noted that a signal amplifier cannot follow high-speed switching unlike a signal attenuator, resulting in the unavoidable need for reducing the switching speed. This certainly results in a substantial reduction in the efficiency of inspection. More-over, when signal amplifiers are used, noise which enters upon performance of an inspection is amplified by a different amplification degree from one channel to another. This leads to undesirous results. It is therefore disadvantageous to adopt signal amplifiers instead of signal attenuators.

Since the minimum value $K_{min}$ was used as a reference in the present embodiment, the description was limited to the example in which the degree of amplification was increased by the value $\Delta d$ in the processing of Procedure $H_7$. This value can, however, be determined suitable in view of various conditions. The processing for increasing the degree of amplification can be skipped provided that data of a sufficient level can be obtained. Although the minimum value $K_{min}$ was used as a reference in the illustrated example, it is possible to use as a reference a value smaller than the minimum value $K_{min}$.

Figure 18:
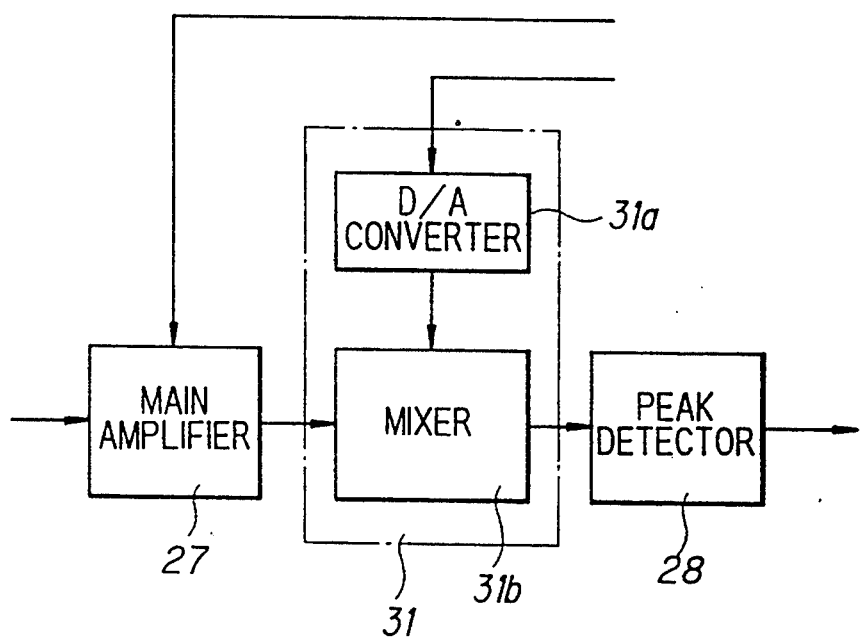
FIG. 18 is a block diagram of a second specific example of a sensitivity equalizer illustrated in FIG. 15.

Another specific example of the sensitivity equalizer 31 will next be described. FIG. 18 is a block diagram of the second specific example of the sensitivity equalizer 31. In the figure, numeral 31a indicates a D/A converter for converting each corrected datum, which has been outputted from CPU 20a'' via the interface 20c, into an analog value whereas numeral 31b designates a mixer for receiving a signal from the main amplifier 27 and multiplying it by the value from the D/A converter.

As has been mentioned above in the description of the preceding specific example, the attenuation factors $G_i$ of the individual channels are calculated by computation pursuant to the formula (5) in the course of the preparation work and are then converted into 8-bit codes based on the attenuation factors set for the signal attenuators $E_1$-$E_8$, respectively. In the present specific example, attenuation factors obtained in accordance with the following formula (6) instead of formula (5) are stored in a suitable memory of the signal processor 20.

$$G_i' = \frac{K_{min}}{K_i} \quad (6)$$

Namely, the minimum value $K_{min}$ is found out from the data which have been obtained by electronically scanning the reference material along a single line. Using the minimum value $K_{min}$ as a reference, the ratios ($K_{min}/K_i$) of the reference value to the data of the individual channels, said data being represented by $K_i$, are computed to equalize the data of the individual channels. These ratios are stored as attenuation ratios $G_i'$ of the individual channels in the suitable memory of the signal processor 20.

Upon ultrasonic inspection of an object, the attenuation factor $G_i'$ of each channel is read from the memory for the signal outputted from the main amplifier 27 subsequent to its reception through the same channel. The attenuation factor is then outputted as an analog value (d.c. signal) via the D/A converter 31a, and both the analog value and the signal are multiplied at the mixer 31b. As a result, it is also possible to eliminate any differences in sensitivity among the individual channels in the present specific example as in the preceding specific example.

As has been described above, according to the first aspect of this invention, inspection data are multiplied by the inverses of ratios of reference data obtained from a reference material through respective channels to their average value, respectively, to obtain corrected data. It is, therefore, possible to eliminate any deleterious influence which may be given due to scattering in sensitivity among the individual channels and to clearly display only an ultrasonic image of a defective portion. As a consequence, an inspection of an object can be performed accurately.

According to the second aspect of this invention, the attenuation factors of individual channels are determined such that reference data obtained from a reference material through the respective channels can be brought to the minimum value of these reference data or to a predetermined constant value smaller than the minimum value, and inspection data are corrected channel by channel on the basis of these attenuation factors, respectively. Therefore, the second aspect of the present invention can exhibit the same advantageous effects as the first aspect of the present invention.

INDUSTRIAL APPLICABILITY

As has been described above, the present invention can be applied to ultrasonic inspection systems of any types as long as they employ array element oscillators.

We claim:
1. An ultrasonic inspection system comprising:
    an array probe having a number of array element oscillators arranged in at least one row, at least some of said oscillators being transmit oscillators for transmitting radiating ultrasonic waves, and at least some of said oscillators being receive oscillators for receiving any reflected waves reflected from an object and then converting the reflected waves into a data signal,
    a memory unit for receiving and storing said data signals from said oscillators obtained by ultrasonic scanning of a surface of an object by the array probe,
    a display unit for showing an ultrasonic image based on the data stored in the memory unit,
    first computing means for computing an average value of individual reference data obtained by said oscillators of the array probe during ultrasonic scanning of a reference material of defect-free uniform quality, each said individual reference datum and said average value being stored in said memory unit,
    second computing means for multiplying individual inspection date of a test object obtained by ultra- sonic scanning of the test object by the array probe with the average value and the inverse of the reference data corresponding to the inspection data; and output means for outputting the results of the computation by the second computing means to the display unit so that a corrected ultrasonic image is displayed.

2. The ultrasonic inspection system of claim 1, wherein the computation by the second computing means is performed upon sampling each of the inspection data of the test object.

3. The ultrasonic inspection system of claim 1, wherein the second computing means first calculates the product of the average value and the inverse of each of the reference datum before sampling the individual inspection data.

4. The ultrasonic inspection system of claim 1, wherein each of said number of oscillators are both a transmit oscillator and a receive oscillator.

* * * * *

UNITED STATES PATENT AND TRADEMARK OFFICE
CERTIFICATE OF CORRECTION

PATENT NO. : 5,331,855
DATED : July 26, 1994
INVENTOR(S) : Yoshihiko TAKISHITA et al.

It is certified that error appears in the above-indentified patent and that said Letters Patent is hereby corrected as shown below:

On the title page,
item 75, change "Takashita" to --Takishita--.

Signed and Sealed this

Eighth Day of November, 1994

Attest:

BRUCE LEHMAN

Attesting Officer

Commissioner of Patents and Trademarks